United States Patent
Möller et al.

(10) Patent No.: US 12,398,427 B2
(45) Date of Patent: *Aug. 26, 2025

(54) CIRCULATING SERUM MICRORNA BIOMARKERS AND METHODS FOR ALZHEIMER'S DISEASE DIAGNOSIS

(71) Applicant: ST. JOHN'S UNIVERSITY, Queens, NY (US)

(72) Inventors: Simon Geir Möller, Queens, NY (US); Ketan Shirish Patil, Queens, NY (US); Guido Werner Alves, Stavanger (NO)

(73) Assignee: ST. JOHN'S UNIVERSITY, Queens, NY (US)

( * ) Notice: Subject to any disclaimer, the term of this patent is extended or adjusted under 35 U.S.C. 154(b) by 12 days.

This patent is subject to a terminal disclaimer.

(21) Appl. No.: 18/182,868

(22) Filed: Mar. 13, 2023

(65) Prior Publication Data

US 2024/0209444 A1 Jun. 27, 2024

Related U.S. Application Data

(62) Division of application No. 16/623,937, filed as application No. PCT/US2018/036377 on Jun. 7, 2018, now Pat. No. 11,634,775.

(60) Provisional application No. 62/521,768, filed on Jun. 19, 2017.

(51) Int. Cl.
*C12Q 1/6883* (2018.01)

(52) U.S. Cl.
CPC ..... *C12Q 1/6883* (2013.01); *C12Q 2600/158* (2013.01); *C12Q 2600/178* (2013.01); *G01N 2800/2821* (2013.01)

(58) Field of Classification Search
None
See application file for complete search history.

(56) References Cited

U.S. PATENT DOCUMENTS

| | | |
|---|---|---|
| 2012/0108650 A1 | 5/2012 | Jin et al. |
| 2013/0040303 A1 | 2/2013 | Wang |
| 2014/0206777 A1 | 7/2014 | Goren |
| 2014/0378439 A1 | 12/2014 | Dezso |
| 2016/0273043 A1 | 9/2016 | Umanksy |
| 2018/0067132 A1 | 3/2018 | Tahara |

FOREIGN PATENT DOCUMENTS

| | | |
|---|---|---|
| JP | 2014-520529 A | 8/2014 |
| JP | 2016-538851 A | 12/2016 |
| WO | 2009/009457 A1 | 1/2009 |
| WO | 2013/003350 A1 | 1/2013 |
| WO | 2013/022953 A1 | 2/2013 |
| WO | 2013/024469 A1 | 2/2013 |
| WO | 2015/179909 A1 | 12/2015 |
| WO | WO 2015/179909 * | 12/2015 |
| WO | 2016/148073 A1 | 9/2016 |
| WO | 2017/136662 A1 | 8/2017 |
| WO | 2017/165458 A1 | 9/2017 |
| WO | WO 2017/165458 * | 9/2017 |

OTHER PUBLICATIONS

Geekiyanage et al., "Blood serum miRNA: Non-invasive biomarkers for Alzheimer's disease", Experimental Neurology, vol. 235, No. 2 (2012) 491-6.
Li et al., MicroRNA-574 is involved in cognitive impairment in 5-month-old APP/PS1 mice through regulation of neuritin, Brain Research 2015, vol. 1627, pp. 177-188.
Liang et al., Characterization of microRNA expression profiles in normal human tissues, BMC Genomics, 2007, pp. 1-20.
Lugli et al., Plasma Exosomal miRNAs in Persons with and without Alzheimer Disease: Altered Expression and Prospects for Biomarkers, PLOS ONE, DOI: 10.1371, Oct. 2015 pp. 1-18.
Patil et al., Combinatory microRNA serum signatures as classifiers of Parkinson's disease, Parkinson and Related Disorders 64 (2019) pp. 202-210.
Skumikov, et al. Profile of microRNA in Blood Plasma of Healthy Humans, Bulletin of Experimental Biology and Medicine, vol. 160, No. 5, Mar. 2016.
Thisted, What is a P-value? Departments of Statistics and Health Studies, The University of Chicago, May 1998, pp. 1-6.
Wang, Comparing the MicroRNA Spectrum between Serum and Plasma, Institute for Systems Biology, Seattle Washington, PLOS One, vol. 7, Issue 7, Jul. 2012.
Wolenski, Identification of microRNA biomarker candidates in urine and plasma from rats with kidney or liver damage, Journal of Applied Toxicology, 2017; 37; 278-286.
Cheng, L., et al., Prognostic serum miRNA biomarkers associated with Alzheimer's disease shows concordance with neuropsychological and neuroimaging assessment, Molecular Psychiatry, Oct. 28, 2014, pp. 1-9.
Denk, Johannes et al., MicroRNA Profiling of CSF Reveals Potential Biomarkers to Detect Alzheimer's Disease, PLOS One, vol. 10, No. 5, May 20, 2015, pp. 1-18.
Kumar, Subodh et al., Are circulating microRNAs peripheral biomarkers for Alzheimer's disease? Biochimica et Biophysica Acta vol. 1862, No. 9, Jun. 2, 2016, pp. 1617-1627.

* cited by examiner

*Primary Examiner* — Amanda Haney
(74) *Attorney, Agent, or Firm* — VENABLE LLP

(57) ABSTRACT

Biomarkers and methods for identifying, verifying and confirming circulating serum-based microRNAs. The microRNAs (PARKmiRs) can be used to differentiate patient's suffering from Alzheimer's disease (AD) from non-AD patients.

34 Claims, 2 Drawing Sheets

Specification includes a Sequence Listing.

```
                           SEQUENCE LISTING

Sequence total quantity: 88
SEQ ID NO: 1             moltype = RNA  length = 22
FEATURE                  Location/Qualifiers
source                   1..22
                         mol_type = unassigned RNA
                         organism = Homo sapiens
SEQUENCE: 1
tcaccgggtg taaatcagct tg                                                22

SEQ ID NO: 2             moltype = RNA  length = 79
FEATURE                  Location/Qualifiers
source                   1..79
                         mol_type = unassigned RNA
                         organism = Homo sapiens
SEQUENCE: 2
cccgggctga ggtaggaggt tgtatagttg aggaggacac ccaaggagat cactatacgg       60
cctcctagct ttccccagg                                                    79

SEQ ID NO: 3             moltype = RNA  length = 23
FEATURE                  Location/Qualifiers
source                   1..23
                         mol_type = unassigned RNA
                         organism = Homo sapiens
SEQUENCE: 3
cctgcagcga cttgatggct tcc                                               23

SEQ ID NO: 4             moltype = RNA  length = 111
FEATURE                  Location/Qualifiers
source                   1..111
                         mol_type = unassigned RNA
                         organism = Homo sapiens
SEQUENCE: 4
ccacggtcct agttaaaaag gcacattcct agaccctgcc tcagaactac tgaacagagt       60
cactgggtgt ggagtccagg aatctgcatt tttaccccta tcgcccccgc c                111

SEQ ID NO: 5             moltype = RNA  length = 22
FEATURE                  Location/Qualifiers
source                   1..22
                         mol_type = unassigned RNA
                         organism = Homo sapiens
SEQUENCE: 5
tcaaaactga ggggcatttt ct                                                22

SEQ ID NO: 6             moltype = RNA  length = 22
FEATURE                  Location/Qualifiers
source                   1..22
                         mol_type = unassigned RNA
                         organism = Homo sapiens
SEQUENCE: 6
gctatttcac gacaccaggg tt                                                22

SEQ ID NO: 7             moltype = RNA  length = 22
FEATURE                  Location/Qualifiers
source                   1..22
                         mol_type = unassigned RNA
                         organism = Homo sapiens
SEQUENCE: 7
ctcctacata ttagcattaa ca                                                22

SEQ ID NO: 8             moltype = RNA  length = 22
FEATURE                  Location/Qualifiers
source                   1..22
                         mol_type = unassigned RNA
                         organism = Homo sapiens
SEQUENCE: 8
```

-continued

```
ccaatattac tgtgctgctt ta                                          22

SEQ ID NO: 9             moltype = RNA   length = 23
FEATURE                  Location/Qualifiers
source                   1..23
                         mol_type = unassigned RNA
                         organism = Homo sapiens
SEQUENCE: 9
aacattcatt gctgtcggtg ggt                                         23

SEQ ID NO: 10            moltype = RNA   length = 21
FEATURE                  Location/Qualifiers
source                   1..21
                         mol_type = unassigned RNA
                         organism = Homo sapiens
SEQUENCE: 10
ctatatatca aacatattcc t                                           21

SEQ ID NO: 11            moltype = RNA   length = 21
FEATURE                  Location/Qualifiers
source                   1..21
                         mol_type = unassigned RNA
                         organism = Homo sapiens
SEQUENCE: 11
atgacctatg aattgacaga c                                           21

SEQ ID NO: 12            moltype = RNA   length = 22
FEATURE                  Location/Qualifiers
source                   1..22
                         mol_type = unassigned RNA
                         organism = Homo sapiens
SEQUENCE: 12
acctggcata caatgtagat tt                                          22

SEQ ID NO: 13            moltype = RNA   length = 24
FEATURE                  Location/Qualifiers
source                   1..24
                         mol_type = unassigned RNA
                         organism = Homo sapiens
SEQUENCE: 13
agcgcgggct gagcgctgcc agtc                                        24

SEQ ID NO: 14            moltype = RNA   length = 21
FEATURE                  Location/Qualifiers
source                   1..21
                         mol_type = unassigned RNA
                         organism = Homo sapiens
SEQUENCE: 14
atccccagat acaatggaca a                                           21

SEQ ID NO: 15            moltype = RNA   length = 22
FEATURE                  Location/Qualifiers
source                   1..22
                         mol_type = unassigned RNA
                         organism = Homo sapiens
SEQUENCE: 15
tggtttaccg tcccacatac at                                          22

SEQ ID NO: 16            moltype = RNA   length = 23
FEATURE                  Location/Qualifiers
source                   1..23
                         mol_type = unassigned RNA
                         organism = Homo sapiens
SEQUENCE: 16
ctgactgaat aggtagggtc att                                         23

SEQ ID NO: 17            moltype = RNA   length = 86
FEATURE                  Location/Qualifiers
source                   1..86
                         mol_type = unassigned RNA
                         organism = Homo sapiens
SEQUENCE: 17
gagggaaagc aggccaacct cgaggatctc cccagccttg gcgttcaggt gctgaggaga 60
tcgtcgaggt tggcctgctt cccctc                                      86

SEQ ID NO: 18            moltype = RNA   length = 85
FEATURE                  Location/Qualifiers
source                   1..85
                         mol_type = unassigned RNA
```

```
                        organism = Homo sapiens
SEQUENCE: 18
ggacctgccc tgggctttct agtctcagct ctcctccagc tcagctggtc aggagagctg    60
agactagaaa gcccagggca ggttc                                          85

SEQ ID NO: 19           moltype = RNA   length = 81
FEATURE                 Location/Qualifiers
source                  1..81
                        mol_type = unassigned RNA
                        organism = Homo sapiens
SEQUENCE: 19
acctgccctg ggctttctag tctcagctct cctgaccagc tgagctggag gagagctgag    60
actagaaagc ccagggcagg t                                              81

SEQ ID NO: 20           moltype = RNA   length = 85
FEATURE                 Location/Qualifiers
source                  1..85
                        mol_type = unassigned RNA
                        organism = Homo sapiens
SEQUENCE: 20
ggcgcctcct gctctgctgt gccgccaggg cctcccctag cgcgccttct ggagaggctt    60
tgtgcggata cggggctgga ggcct                                          85

SEQ ID NO: 21           moltype = RNA   length = 79
FEATURE                 Location/Qualifiers
source                  1..79
                        mol_type = unassigned RNA
                        organism = Homo sapiens
SEQUENCE: 21
aattaatccc tctctttcta gttcttccta gagtgaggaa aagctgggtt gagagggcaa    60
acaaattaac taattaatt                                                 79

SEQ ID NO: 22           moltype = RNA   length = 23
FEATURE                 Location/Qualifiers
source                  1..23
                        mol_type = unassigned RNA
                        organism = Homo sapiens
SEQUENCE: 22
tcaagagcaa taacgaaaaa tgt                                            23

SEQ ID NO: 23           moltype = RNA   length = 98
FEATURE                 Location/Qualifiers
source                  1..98
                        mol_type = unassigned RNA
                        organism = Homo sapiens
SEQUENCE: 23
acccaaaccc taggtctgct gactcctagt ccagggctcg tgatggctgg tgggccctga    60
acgagggggtc tggaggcctg ggtttgaata tcgacagc                           98

SEQ ID NO: 24           moltype = RNA   length = 23
FEATURE                 Location/Qualifiers
source                  1..23
                        mol_type = unassigned RNA
                        organism = Homo sapiens
SEQUENCE: 24
taggcagtgt cattagctga ttg                                            23

SEQ ID NO: 25           moltype = RNA   length = 24
FEATURE                 Location/Qualifiers
source                  1..24
                        mol_type = unassigned RNA
                        organism = Homo sapiens
SEQUENCE: 25
acaaaaaaaa aagcccaacc cttc                                           24

SEQ ID NO: 26           moltype = RNA   length = 92
FEATURE                 Location/Qualifiers
source                  1..92
                        mol_type = unassigned RNA
                        organism = Homo sapiens
SEQUENCE: 26
tgtcactccg ccagcatcat gaagtgcact catgatatgt tgccccatc agcgtgtcac     60
gagggcattt catgatgcag gcggggttgg ca                                  92

SEQ ID NO: 27           moltype = RNA   length = 22
FEATURE                 Location/Qualifiers
source                  1..22
                        mol_type = unassigned RNA
                        organism = Homo sapiens
```

```
SEQUENCE: 27
ctgggaggtg tgatatcgtg gt                                              22

SEQ ID NO: 28           moltype = RNA    length = 19
FEATURE                 Location/Qualifiers
source                  1..19
                        mol_type = unassigned RNA
                        organism = Homo sapiens
SEQUENCE: 28
actggacttg gaggcagaa                                                  19

SEQ ID NO: 29           moltype = RNA    length = 111
FEATURE                 Location/Qualifiers
source                  1..111
                        mol_type = unassigned RNA
                        organism = Homo sapiens
SEQUENCE: 29
cttttgctgt cagttttttct gttgcttgtc ttggttttat gcctttata tcaaggcaca     60
taaaaggcat aaaaccaaga caagcaacaa aaaaaggatt gatcacagaa g              111

SEQ ID NO: 30           moltype = RNA    length = 22
FEATURE                 Location/Qualifiers
source                  1..22
                        mol_type = unassigned RNA
                        organism = Homo sapiens
SEQUENCE: 30
tcaggtgtgg aaactgaggc ag                                              22

SEQ ID NO: 31           moltype = RNA    length = 17
FEATURE                 Location/Qualifiers
source                  1..17
                        mol_type = unassigned RNA
                        organism = Homo sapiens
SEQUENCE: 31
tggagagaaa ggcagta                                                    17

SEQ ID NO: 32           moltype = RNA    length = 20
FEATURE                 Location/Qualifiers
source                  1..20
                        mol_type = unassigned RNA
                        organism = Homo sapiens
SEQUENCE: 32
agccccctgg ccccaaaccc                                                 20

SEQ ID NO: 33           moltype = RNA    length = 18
FEATURE                 Location/Qualifiers
source                  1..18
                        mol_type = unassigned RNA
                        organism = Homo sapiens
SEQUENCE: 33
ttgcacttgt ctcagtga                                                   18

SEQ ID NO: 34           moltype = RNA    length = 94
FEATURE                 Location/Qualifiers
source                  1..94
                        mol_type = unassigned RNA
                        organism = Homo sapiens
SEQUENCE: 34
tggtttgcga ctctgaaaac tagaaggttt atgactgggc atttctcacc caatgcccaa     60
tattgaactt tctagttgtc agagtcatta accc                                 94

SEQ ID NO: 35           moltype = RNA    length = 70
FEATURE                 Location/Qualifiers
source                  1..70
                        mol_type = unassigned RNA
                        organism = Homo sapiens
SEQUENCE: 35
ttcctgcaga ttgtttctttt tgccgtgcaa gtttaagttt ttgcacggca aagaaacaa     60
tccagagggt                                                            70

SEQ ID NO: 36           moltype = RNA    length = 73
FEATURE                 Location/Qualifiers
source                  1..73
                        mol_type = unassigned RNA
                        organism = Homo sapiens
SEQUENCE: 36
actgtccttc agccagagct ggctgaaggg cagaagggaa ctgtccttca gccagagctg     60
gctgaagggc aga                                                        73
```

```
SEQ ID NO: 37            moltype = RNA  length = 22
FEATURE                  Location/Qualifiers
source                   1..22
                         mol_type = unassigned RNA
                         organism = Homo sapiens
SEQUENCE: 37
ttttgcaata tgttcctgaa ta                                                    22

SEQ ID NO: 38            moltype = RNA  length = 21
FEATURE                  Location/Qualifiers
source                   1..21
                         mol_type = unassigned RNA
                         organism = Homo sapiens
SEQUENCE: 38
gcagtccatg ggcatataca c                                                     21

SEQ ID NO: 39            moltype = RNA  length = 81
FEATURE                  Location/Qualifiers
source                   1..81
                         mol_type = unassigned RNA
                         organism = Homo sapiens
SEQUENCE: 39
ggctgcttct cgcctctgtc cagctgtgtg gccttggaca agcctcttgg ttacacagct           60
ggacagaggc acgaaacagc c                                                     81

SEQ ID NO: 40            moltype = RNA  length = 26
FEATURE                  Location/Qualifiers
source                   1..26
                         mol_type = unassigned RNA
                         organism = Homo sapiens
SEQUENCE: 40
cccagggctt ggagtggggc aaggtt                                                26

SEQ ID NO: 41            moltype = RNA  length = 22
FEATURE                  Location/Qualifiers
source                   1..22
                         mol_type = unassigned RNA
                         organism = Homo sapiens
SEQUENCE: 41
agcaaggcgg catctctctg at                                                    22

SEQ ID NO: 42            moltype = RNA  length = 22
FEATURE                  Location/Qualifiers
source                   1..22
                         mol_type = unassigned RNA
                         organism = Homo sapiens
SEQUENCE: 42
tgcggggaca ggccagggca tc                                                    22

SEQ ID NO: 43            moltype = RNA  length = 22
FEATURE                  Location/Qualifiers
source                   1..22
                         mol_type = unassigned RNA
                         organism = Homo sapiens
SEQUENCE: 43
tctgccatcc tccctcccct ac                                                    22

SEQ ID NO: 44            moltype = RNA  length = 21
FEATURE                  Location/Qualifiers
source                   1..21
                         mol_type = unassigned RNA
                         organism = Homo sapiens
SEQUENCE: 44
agcagacttg acctacaatt a                                                     21

SEQ ID NO: 45            moltype = RNA  length = 80
FEATURE                  Location/Qualifiers
source                   1..80
                         mol_type = unassigned RNA
                         organism = Homo sapiens
SEQUENCE: 45
aatgaaggat tacggaccag ctaagggagg cattaggatc cttattcttg cctcccttag           60
ttggtcccta atccttcgtt                                                       80

SEQ ID NO: 46            moltype = RNA  length = 18
FEATURE                  Location/Qualifiers
source                   1..18
                         mol_type = unassigned RNA
                         organism = Homo sapiens
```

| | | |
|---|---|---|
| SEQUENCE: 46 | | |
| tggatatgat gactgaaa | | 18 |
| | | |
| SEQ ID NO: 47 | moltype = RNA   length = 21 | |
| FEATURE | Location/Qualifiers | |
| source | 1..21 | |
| | mol_type = unassigned RNA | |
| | organism = Homo sapiens | |
| SEQUENCE: 47 | | |
| gacagagtgc cacttactga a | | 21 |
| | | |
| SEQ ID NO: 48 | moltype = RNA   length = 22 | |
| FEATURE | Location/Qualifiers | |
| source | 1..22 | |
| | mol_type = unassigned RNA | |
| | organism = Homo sapiens | |
| SEQUENCE: 48 | | |
| atgcacctgg gcaaggattc tg | | 22 |
| | | |
| SEQ ID NO: 49 | moltype = RNA   length = 22 | |
| FEATURE | Location/Qualifiers | |
| source | 1..22 | |
| | mol_type = unassigned RNA | |
| | organism = Homo sapiens | |
| SEQUENCE: 49 | | |
| tgattggtac gtctgtgggt ag | | 22 |
| | | |
| SEQ ID NO: 50 | moltype = RNA   length = 22 | |
| FEATURE | Location/Qualifiers | |
| source | 1..22 | |
| | mol_type = unassigned RNA | |
| | organism = Homo sapiens | |
| SEQUENCE: 50 | | |
| tactcaggag agtggcaatc ac | | 22 |
| | | |
| SEQ ID NO: 51 | moltype = RNA   length = 21 | |
| FEATURE | Location/Qualifiers | |
| source | 1..21 | |
| | mol_type = unassigned RNA | |
| | organism = Homo sapiens | |
| SEQUENCE: 51 | | |
| ctccagaggg aagtactttc t | | 21 |
| | | |
| SEQ ID NO: 52 | moltype = RNA   length = 90 | |
| FEATURE | Location/Qualifiers | |
| source | 1..90 | |
| | mol_type = unassigned RNA | |
| | organism = Homo sapiens | |
| SEQUENCE: 52 | | |
| tcccatgctg tgaccctcta gaggaagcac tttctgtttg ttgtctgaga aaaaacaaag | | 60 |
| tgcttccctt tagagtgtta ccgtttggga | | 90 |
| | | |
| SEQ ID NO: 53 | moltype = RNA   length = 88 | |
| FEATURE | Location/Qualifiers | |
| source | 1..88 | |
| | mol_type = unassigned RNA | |
| | organism = Homo sapiens | |
| SEQUENCE: 53 | | |
| tcccatgctg tgaccctcta gaggaagcac tttctgtttg ttgtctgaga aaaaacaaag | | 60 |
| tgcttccctt tagagttact gtttggga | | 88 |
| | | |
| SEQ ID NO: 54 | moltype = RNA   length = 91 | |
| FEATURE | Location/Qualifiers | |
| source | 1..91 | |
| | mol_type = unassigned RNA | |
| | organism = Homo sapiens | |
| SEQUENCE: 54 | | |
| cgacttgctt tctctcctcc atgccttgag tgtaggaccg ttggcatctt aattaccctc | | 60 |
| ccacacccaa ggcttgcaga agagcgagcc t | | 91 |
| | | |
| SEQ ID NO: 55 | moltype = RNA   length = 25 | |
| FEATURE | Location/Qualifiers | |
| source | 1..25 | |
| | mol_type = unassigned RNA | |
| | organism = Homo sapiens | |
| SEQUENCE: 55 | | |
| aaaaaccaca attactttg cacca | | 25 |
| | | |
| SEQ ID NO: 56 | moltype = RNA   length = 22 | |

```
FEATURE              Location/Qualifiers
source               1..22
                     mol_type = unassigned RNA
                     organism = Homo sapiens
SEQUENCE: 56
caaaaaccgg caattacttt tg                                           22

SEQ ID NO: 57        moltype = RNA  length = 21
FEATURE              Location/Qualifiers
source               1..21
                     mol_type = unassigned RNA
                     organism = Homo sapiens
SEQUENCE: 57
caaaaactgc aattactttc a                                            21

SEQ ID NO: 58        moltype = RNA  length = 21
FEATURE              Location/Qualifiers
source               1..21
                     mol_type = unassigned RNA
                     organism = Homo sapiens
SEQUENCE: 58
aaaggtaatt gtggtttctg c                                            21

SEQ ID NO: 59        moltype = RNA  length = 21
FEATURE              Location/Qualifiers
source               1..21
                     mol_type = unassigned RNA
                     organism = Homo sapiens
SEQUENCE: 59
taaaaactgc aattactttt a                                            21

SEQ ID NO: 60        moltype = RNA  length = 19
FEATURE              Location/Qualifiers
source               1..19
                     mol_type = unassigned RNA
                     organism = Homo sapiens
SEQUENCE: 60
aaaaaccaca attactttt                                               19

SEQ ID NO: 61        moltype = RNA  length = 54
FEATURE              Location/Qualifiers
source               1..54
                     mol_type = unassigned RNA
                     organism = Homo sapiens
SEQUENCE: 61
aaaagtaatt gcggttttg ctattggttt taatggcagt tacttttgca ccag         54

SEQ ID NO: 62        moltype = RNA  length = 22
FEATURE              Location/Qualifiers
source               1..22
                     mol_type = unassigned RNA
                     organism = Homo sapiens
SEQUENCE: 62
aaaagtactt gcggattttg ct                                           22

SEQ ID NO: 63        moltype = RNA  length = 25
FEATURE              Location/Qualifiers
source               1..25
                     mol_type = unassigned RNA
                     organism = Homo sapiens
SEQUENCE: 63
aaaaaccaca attactttg cacca                                         25

SEQ ID NO: 64        moltype = RNA  length = 20
FEATURE              Location/Qualifiers
source               1..20
                     mol_type = unassigned RNA
                     organism = Homo sapiens
SEQUENCE: 64
taaaaactgc aattactttc                                              20

SEQ ID NO: 65        moltype = RNA  length = 110
FEATURE              Location/Qualifiers
source               1..110
                     mol_type = unassigned RNA
                     organism = Homo sapiens
SEQUENCE: 65
gcctaaacta ttaggttggt gcaaaagtaa tcactgtttt tgccattact ctcagtggca  60
aaaccgtga ttacttttgc accaacctag taacacctta actgtgggg             110
```

```
SEQ ID NO: 66              moltype = RNA   length = 97
FEATURE                    Location/Qualifiers
source                     1..97
                           mol_type = unassigned RNA
                           organism = Homo sapiens
SEQUENCE: 66
cttcatccac cagtcctcca ggaacatcaa ggatctttaaa ctttgccaga gctacaaagg      60
caaagtttaa gatccttgaa gttcctgggg gaaccat                                97

SEQ ID NO: 67              moltype = RNA   length = 22
FEATURE                    Location/Qualifiers
source                     1..22
                           mol_type = unassigned RNA
                           organism = Homo sapiens
SEQUENCE: 67
cacacactgc aattactttt gc                                                22

SEQ ID NO: 68              moltype = RNA   length = 21
FEATURE                    Location/Qualifiers
source                     1..21
                           mol_type = unassigned RNA
                           organism = Homo sapiens
SEQUENCE: 68
aaactactga aaatcaaaga t                                                 21

SEQ ID NO: 69              moltype = RNA   length = 95
FEATURE                    Location/Qualifiers
source                     1..95
                           mol_type = unassigned RNA
                           organism = Homo sapiens
SEQUENCE: 69
gacaccacat gctcctccag gcctgcctgc cctccaggtc atgttccagt gtcccacaga       60
tgcagcacca cggcccaggc ggcattggtg tcacc                                  95

SEQ ID NO: 70              moltype = RNA   length = 97
FEATURE                    Location/Qualifiers
source                     1..97
                           mol_type = unassigned RNA
                           organism = Homo sapiens
SEQUENCE: 70
ccaccacggt gctggcacca gggcctctgc cccgtaggac accgaggctt atgaatagga       60
gcagtgccgg ccaaggcgcc ggcaccatct tggtgat                                97

SEQ ID NO: 71              moltype = RNA   length = 22
FEATURE                    Location/Qualifiers
source                     1..22
                           mol_type = unassigned RNA
                           organism = Homo sapiens
SEQUENCE: 71
tgggaaagag aaagaacaag ta                                                22

SEQ ID NO: 72              moltype = RNA   length = 22
FEATURE                    Location/Qualifiers
source                     1..22
                           mol_type = unassigned RNA
                           organism = Homo sapiens
SEQUENCE: 72
tcgggcctgg ggttgggga gc                                                 22

SEQ ID NO: 73              moltype = RNA   length = 59
FEATURE                    Location/Qualifiers
source                     1..59
                           mol_type = unassigned RNA
                           organism = Homo sapiens
SEQUENCE: 73
cgggctctgg gtgcagtggg ggttcccacg ccgcggcaac caccactgtc tctccccag        59

SEQ ID NO: 74              moltype = RNA   length = 25
FEATURE                    Location/Qualifiers
source                     1..25
                           mol_type = unassigned RNA
                           organism = Homo sapiens
SEQUENCE: 74
taggggtggg ggaattcagg ggtgt                                             25

SEQ ID NO: 75              moltype = RNA   length = 20
FEATURE                    Location/Qualifiers
source                     1..20
```

```
                        mol_type = unassigned RNA
                        organism = Homo sapiens
SEQUENCE: 75
tccccaaccc ctgcccgcag                                                  20

SEQ ID NO: 76           moltype = RNA   length = 61
FEATURE                 Location/Qualifiers
source                  1..61
                        mol_type = unassigned RNA
                        organism = Homo sapiens
SEQUENCE: 76
gtgcggaacg ctggccgggg cgggaggggA agggacgccc ggccggaacg ccgcactcac       60
g                                                                      61

SEQ ID NO: 77           moltype = RNA   length = 21
FEATURE                 Location/Qualifiers
source                  1..21
                        mol_type = unassigned RNA
                        organism = Homo sapiens
SEQUENCE: 77
acaccctctt tccctaccgc c                                                21

SEQ ID NO: 78           moltype = RNA   length = 22
FEATURE                 Location/Qualifiers
source                  1..22
                        mol_type = unassigned RNA
                        organism = Homo sapiens
SEQUENCE: 78
cagagggaat acagagggca at                                               22

SEQ ID NO: 79           moltype = RNA   length = 67
FEATURE                 Location/Qualifiers
source                  1..67
                        mol_type = unassigned RNA
                        organism = Homo sapiens
SEQUENCE: 79
tggagctgtg tgcagggcca gcgcggagcc cgagcagccg cggtgaagcg cctgtgctct       60
gccgaga                                                                67

SEQ ID NO: 80           moltype = RNA   length = 20
FEATURE                 Location/Qualifiers
source                  1..20
                        mol_type = unassigned RNA
                        organism = Homo sapiens
SEQUENCE: 80
tgtgaccta gaataattac                                                   20

SEQ ID NO: 81           moltype = RNA   length = 22
FEATURE                 Location/Qualifiers
source                  1..22
                        mol_type = unassigned RNA
                        organism = Homo sapiens
SEQUENCE: 81
cgggactgta gagggcatga gc                                               22

SEQ ID NO: 82           moltype = RNA   length = 80
FEATURE                 Location/Qualifiers
source                  1..80
                        mol_type = unassigned RNA
                        organism = Homo sapiens
SEQUENCE: 82
ccttgctgat ggcagatgtc ggatctgcct cgcttatacg tgcccttgct gatggcagat       60
gtcgggtctg cctcgcttat                                                  80

SEQ ID NO: 83           moltype = RNA   length = 82
FEATURE                 Location/Qualifiers
source                  1..82
                        mol_type = unassigned RNA
                        organism = Homo sapiens
SEQUENCE: 83
aaggagcact cactccaatt tccctggact gggggcaggc tgccacctcc tggggacagg       60
ggattggggc aggatgttcc ag                                               82

SEQ ID NO: 84           moltype = RNA   length = 77
FEATURE                 Location/Qualifiers
source                  1..77
                        mol_type = unassigned RNA
                        organism = Homo sapiens
SEQUENCE: 84
```

```
tgcaatgccc tactcagaaa ggtgccattt atgtagattt tatgtcactg gctcctttct    60
gggtagagca aggctca                                                   77

SEQ ID NO: 85           moltype = RNA  length = 22
FEATURE                 Location/Qualifiers
source                  1..22
                        mol_type = unassigned RNA
                        organism = Homo sapiens
SEQUENCE: 85
acagtagagg gaggaatcgc ag                                             22

SEQ ID NO: 86           moltype = RNA  length = 20
FEATURE                 Location/Qualifiers
source                  1..20
                        mol_type = unassigned RNA
                        organism = Homo sapiens
SEQUENCE: 86
gtgagtcagg gtggggctgg                                                20

SEQ ID NO: 87           moltype = RNA  length = 69
FEATURE                 Location/Qualifiers
source                  1..69
                        mol_type = unassigned RNA
                        organism = Homo sapiens
SEQUENCE: 87
agaggcttgg gccgccgagc tggacccgga ccggttttgg gtactgtact gggggcaggg    60
cagagaggg                                                            69

SEQ ID NO: 88           moltype = RNA  length = 106
FEATURE                 Location/Qualifiers
source                  1..106
                        mol_type = unassigned RNA
                        organism = Homo sapiens
SEQUENCE: 88
gtgctcgctt cggcagcaca tatactaaaa ttggaacgat acagagaaga ttagcatggc    60
ccctgcgcaa ggatgacacg caaattcgtg aagcgttcca tatttt                  106
```

CIRCULATING SERUM MICRORNA BIOMARKERS AND METHODS FOR ALZHEIMER'S DISEASE DIAGNOSIS

BACKGROUND OF THE INVENTION

This application is a divisional of U.S. patent application Ser. No. 16/623,937 filed Dec. 18, 2019 which claims benefit of PCT Application No. PCT/US2018/036377 filed Jun. 7, 2018, which in turn claims benefit of U.S. Provisional Application No. 62/521,768 filed Jun. 19, 2017.

The 80,360 bytes Sequence Listing XML file named 140415 576840 SL.xml. created on Jun. 8, 2023 is hereby incorporated by reference. The sequence data presented in the Sequence Listing XML file may be found in Table 1 at specification paragraph [0027], and so that Sequence Listing XML file contains no new matter.

1. Field of the Invention

The present invention generally relates to serum-based microRNAs and methods for differentiating patients suffering from Alzheimer's disease, as well as assisting clinicians to determine treatment protocols for such patients.

2. Brief Description of the Background Art

Alzheimer's disease (AD), the most common neurodegenerative disease, is characterized by loss of memory and other cognitive abilities of an individual with treatment available for only symptomatic relief Alzheimer's is a progressive disease, which advances with increasingly severe symptoms including mood and behavior changes; difficulty speaking, swallowing and walking; disorientation and more serious memory loss. The drug combinations in use are only palliative but cannot reverse the process of neuronal cell death. There are neither any objective tests nor any established biomarkers for the diagnosis of AD. Further, the heterogeneity, subtypes and the progression of the disease makes it even complex to develop specific therapeutic candidates. Thus it is imperative to diagnose disease at the early stage to increase the efficacy of therapeutic agents.

AD and AD related dementia currently affects about 44 million people world-wide. Effective management of a patient with AD is possible in the initial years of treatment, after which time a series of often debilitating complications occur. Current treatment for AD includes multi-drug regiment including cholinesterase inhibitors, Antidepressants, Anxiolytics, Antipsychotic medications, and sedatives to treat a specific symptom. There are many new drugs being developed that can alter the disease process itself by targeting AD-related proteins and processes including beta-amyloid, beta-secretase, Tau-protein, inflammation, and the 5HT6 receptor amongst others.

In the brain, neurons connect and communicate at synapses, where tiny bursts of chemicals called neurotransmitters carry information from one cell to another. Neurons are the chief cells destroyed by Alzheimer's disease. Accordingly, Alzheimer's disease destroys synapses and kills neurons, damaging and eventually destroying the brain's communication network.

Current FDA-approved Alzheimer's drugs support this communication process through two different mechanisms:
1) Cholinesterase inhibitors work by slowing down the process that breaks down a key neurotransmitter. Specifically, cholinesterase inhibitors boost levels of cell-to-cell communication by providing the neurotransmitter acetylcholine that is depleted in the brain by Alzheimer's disease. Donepezil, galantamine and rivastigmine are cholinesterase inhibitors.
2) Memantine is an NMDA (N-methyl-D-aspartate) receptor antagonist and works by regulating the activity of glutamate, a neurotransmitter in the brain. Attachment of glutamate to cell surface NMDA receptors permits calcium to enter the cell. This process is important for cell signaling, as well as learning and memory. In Alzheimer's disease, excess glutamate can be released from damaged cells, leading to chronic overexposure to calcium, which can speed up cell damage. Memantine helps prevent this destructive chain of events by partially blocking the NMDA receptors.

Although the effectiveness of cholinesterase inhibitors and memantine varies widely across the population, it is imperative to diagnose individuals with AD at an early stage to increase the efficacy of therapeutic agents. However, there are neither any objective tests nor established biomarkers for diagnosing AD. Moreover, the heterogeneity, subtypes and progression of the disease make it difficult to develop specific therapeutic candidates.

MicroRNAs ("miRNAs) are a class of non-coding RNAs that play key roles in the regulation of gene expression. miRNAs act at the post-transcriptional level and fine-tune the expression of as much as 30% of all mammalian protein-encoding genes. Mature miRNAs are short, single-stranded RNA molecules approximately 22 nucleotides in length. miRNAs may be encoded by multiple loci, and may be organized in tandemly co-transcribed clusters. miRNA genes are transcribed by RNA polymerase II as large primary transcripts (pri-microRNA) that are processed by a protein complex containing the RNase III enzyme Drosha, DGCR8 and other cofactors, to form an approximately 70 nucleotide precursor microRNA (pre-miRNA). (Cathew R W, Cell, 2009; Kim V N, Nat Rev Mol Cel Biol, 2009; Siomi H, Mol Cel, 2010; Bartel D P, Cell, 2004; Lee Y, Nature 2003; Han J, Genes Dev, 2004.) Pre-miRNA is transported to the cytoplasm by Exportin-5 where it is processed by DICER, a second RNase III enzyme, together with TRBP, PACT and Ago2 in the RNA Induced Silencing Complex resulting in miRNA duplexes (Kim V N, Nat Rev Mol Cel Biol, 2009; Gregory R I, Nature 2004; MAcRae I J, PNAS, 2008). The guide strands of miRNA duplexes separate and associate with Ago 2 for incorporation into a ribonuclear particle to form the RNA-induced silencing complex RISC that mediates gene silencing. The mechanisms of miRNA range from direct degradation or silencing of mRNA and repression of translation to post-transcriptional upregulations. (MacRae I J, PNAS, 2008.)

The presence of miRNAs has been reported in body fluids including blood, cerebrospinal fluid (CSF), plasma, serum and saliva at detectable levels. The tissue-specificity of miRNAs suggests their vital and integral role in various physiological processes. The tissue-enrichment promises a new but less explored role as diagnostic biomarker and potential therapeutic target. Circulating miRNAs are understood to originate from passive leakage from damaged tissue as a result of cell lysis or apoptosis, active transport from cells via microvesicles, such as exosomes, or bound within RISC protein complexes (Etheridge et al, 2011). Exosome and osmotic pump-mediated delivery of small RNA molecules to the brain and CNS, respectively, provides a solution to overcoming the limitations of miRNA-based therapies (Alvarez-Erviti et al., 2011; Koval et al, 2013, Hum. Mol. Gen). miRNA has been demonstrated to be exceptionally stable and thus present as powerful candidates to be potential biomarkers (Chen et al, 2008; Grasso, 2014).

SUMMARY OF THE INVENTION

It is an object of the present invention to identify miRNAs relevant to patients suffering from Alzheimer's disease.

It is another object of the present invention to provide methods for determining patients suffering from Alzheimer's disease.

These objects and others are achieved by the present invention, which provides miRNA biomarkers that may be used singly, in pairs or in combination to determine patients suffering from Alzheimer's disease.

DETAILED DESCRIPTION OF THE INVENTION

Figure 1:
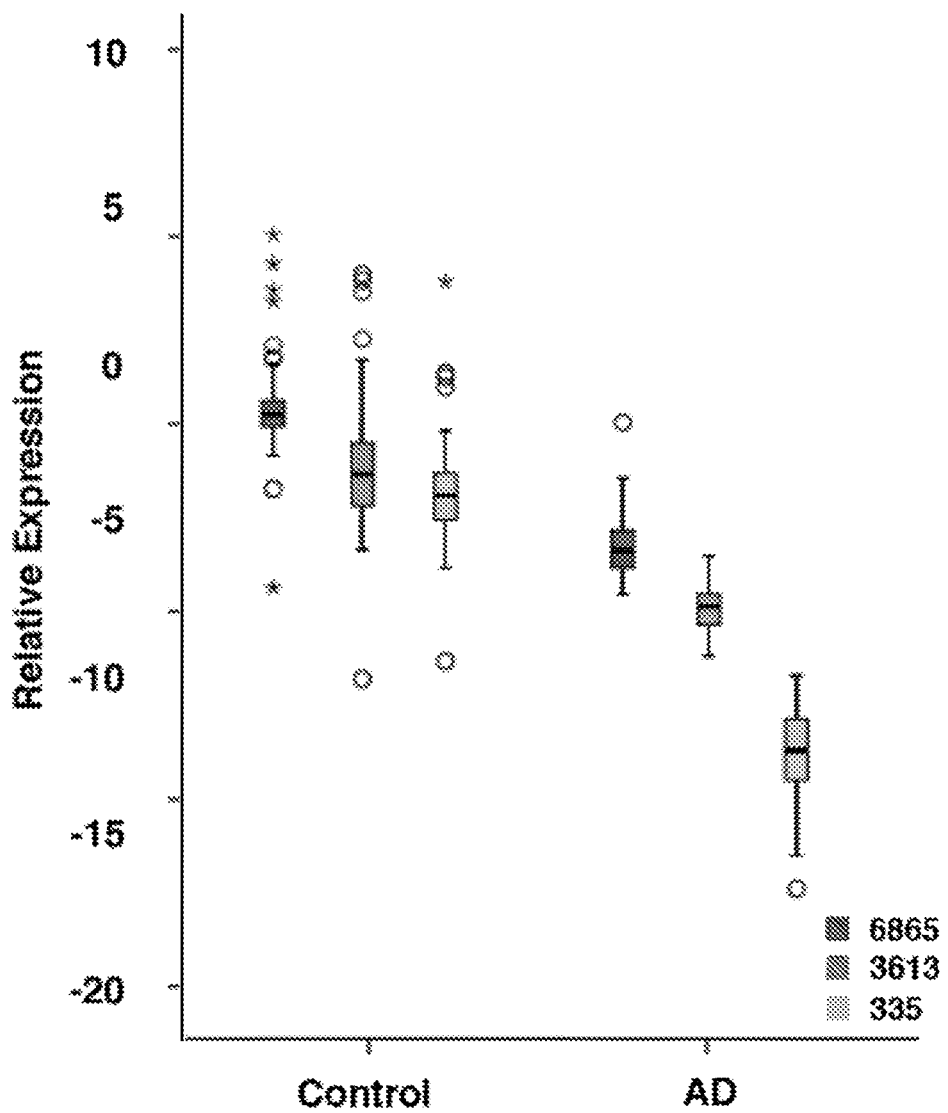
FIG. 1 shows the mean fold change of three PARKmiR-NAs between AD patients and healthy controls.

We performed microarray analysis (discovery phase from the Norwegian ParkWest study), confirmation by qRT-PCR (same samples from discovery phase), verification by qRT-PCR (large sample set from the Norwegian Parkwest study) and validation by qRT-PCR (independent cohort from the Swedish NYPUM study) on control and PD serum samples at baseline as described in the PD diagnostic patent. All this data was generated and discussed in U.S. Application No. 62/291,619 filed Feb. 5, 2016 and International Application No. PCT/US2017/016412 filed Feb. 3, 2017, the disclosures of which are hereby incorporated herein by reference.

During data collection for the diagnostic PD miRNA project we also tested the candidate miRNAs (PARKmiRs) for specificity using 45 serum samples from newly diagnosed AD patients from the DemVest study representing the same region in Norway as for the PD population in the Parkwest study. The inventors expected that the PARKmiRs would show the same abundance levels as in control serum samples, which would verify specificity of the PARKmiRs to PD. Unexpectedly the PARKmiRs showed a significant decrease in levels in the AD serum samples as compared to control serum samples. To ensure that the AD serum samples and the techniques used were valid we tested whether miR-445-3p and control small RNA (U6) changed in abundance. In control serum, PD serum and AD serum both miRNAs remained unchanged in abundance validating our findings.

METHODS

Serum Samples Handling and Classification

All patients and controls participated in the Norwegian ParkWest study and the Dementia Study of Western Norway (DemVest study) which are ongoing prospective population-based longitudinal cohort studies investigating the incidence, neurobiology and prognosis of PD and dementia/AD, respectively. The Norwegian ParkWest study is a prospective longitudinal multicenter cohort study of patients with incident Parkinson's disease (PD) from Western and Southern Norway. Between Nov. 1, 2004 and 31 of Aug. 2006 it was endeavored to recruit all new cases of Parkinson Disease within the study area. Since the start of the study 212 of 265 (80%) of these patients and their age-/sex-matched control group have been followed. The Dementia Study of Western Norway is a prospective longitudinal multicenter cohort study of patients with a first-time dementia diagnosis (Mini Mental State Examination (MMSE) score >15). Patient recruitment started in 2005 and patients were followed annually. Patients with acute delirium or confusion, terminal illness, or current or previous bipolar disorder or psychotic disorder, or who were recently diagnosed with a major somatic illness, were excluded from the study.

All possible efforts were undertaken to establish an unselected and population-representative cohort of patients with AD. Patients were included if they had provided serum at study entry and fulfilled diagnostic criteria for AD according to the National Institute of Neurological and Communicative Diseases and Stroke/Alzheimer's Disease and Related Disorders Association (NINCDS/ARDRA) criteria at latest follow-up. Control subjects were recruited from multiple sources, including friends, spouses, and public organizations for elderly and were included in this study if they had provided serum. In this study of possible biomarkers for AD we applied a two-stage procedure. For the first discovery phase serum from 16 patients and 8 controls were selected at random. The remaining 45 patients with AD and 182 controls that were eligible for this study were selected for verification purposes. Serum samples were collected at the same day as the clinical examinations and then stored frozen at −70 degrees Celsius until transported to the facilities in New York on dry ice.

Example 1: Analyses of Differentially Expressed Human miRNA by qPCR

RNA Isolation from Serum Samples and QC

After thawing on ice, twenty-four (eight control, sixteen PD samples) serum samples were spun down for 5 mins at 3000×g to remove debris. The supernatant was used to perform small RNA isolation using miRCURY RNA Isolation Kit—Biofluids (Exiqon, MA). Before RNA Isolation, the lysis buffer was spiked with 0.267fmol/ul of spike-in control cel-miR-39-3p (Qiagen, CA). The remaining part of the RNA isolation was performed following the manufacturer's protocol and the isolated RNA was quantified on a Nanodrop 2000 (Thermo Scientific, MA). The RNA was used for running Affymetrix v4 microRNA microarray chips and for subsequent cDNA synthesis and qPCR. RNA from 256 serum samples (190 control, 16 PD from ParkWest project 45 AD from the DemVest project) was isolated as described above, they were not quantified by Nanodrop, but the qPCR data resulting from these samples were normalized by a reference small RNA scaRNA17.

miRNA Microarray and Data Analysis

The isolated RNA from twenty-four patient serum samples were quantified and subjected to Affymetrix GeneChip® miRNA 4.0 Array by the Yale Center for Genome Analysis. The normalized.CEL files obtained from Affymetrix Expression Console software were imported into Partek Genomics Suite version 6.6 Copyright © 2012 (Partek, MO) for analysis. The 'microRNA Expression Workflow' was employed to detect differentially expressed miRNAs employing ANOVA resulting in lists of miRNAs significantly (p<0.05) expressed between control versus PD cohorts. The miRNAs detected were used for further qPCR verification.

Quantitative Polymerase Chain Reaction cDNA for miRNA specific qPCR was synthesized using qScript™ microRNA cDNA Synthesis kit (Quanta Biosciences, MD) following manufacturer's protocol and subsequent qPCRs were performed using miRNA specific forward primers (Table #) and PerfeCTa®Universal PCR primer (Quanta Biosciences, MD). scaRNA17 and U6 were used reference small RNAs for normalizing qPCR Cq values whereas cel-miR-39-3p was used as spike-in control. PerfeCTa® SYBR® GREEN SuperMix for IQ™ (Quanta Biosciences, MD) was used for all qPCRs in a MyiQ™ Single color Real-Time PCR Detection System (Bio-Rad, CA). Standard curve for cel-miR-39-3p was analyzed in MS Excel with $R^2=0.97882$ and PCR efficiency 92.96%. No Template Control (NTC) was implied wherever needed.

Data Analysis Based on PD Model

The discriminative ability of miRNAs with regard to PD diagnosis was assessed from ROC analysis using IBM SPSS Statistics, version 21; for combinations of miRNAs the test variable was the predicted probability from logistic regression with PD diagnosis (yes/no) as outcome. To minimize the influence of outlying values on the fit, logistic regression was performed with log transformed miRNA values.

Differentially expressed human miRNAs in PD patients' serum samples from The Norwegian ParkWest study were determined employing miRNA microarray. Provided below are the miRNAs with >1.2 fold differential expression.

85 Differentially Expressed Human Pre- and Mature miRNAs with >1.2 Fold Change hsa-miR-548ac, hsa-miR-335-5p, hsa-miR-548x-3p, hsa-miR-520g, hsa-miR-520h, hsa-miR-548ae, hsa-miR-3910-1, hsa-miR-4708-3p, hsa-miR-16-2-3p, hsa-miR-603, hsa-miR-3613-3p, hsa-miR-4797-5p, hsa-miR-548aj-3p, hsa-miR-450b-5p, hsa-miR-548ap-3p, hsa-miR-1184, hsa-miR-2277-5p, hsa-miR-1323, hsa-miR-548aa, hsa-miR-548t-3p, hsa-miR-221-5p, hsa-miR-190a-3p, hsa-miR-6873-5p, hsa-miR-155-3p, hsa-miR-510-5p, hsa-miR-4313, hsa-miR-3616, hsa-miR-8075, hsa-miR-4306, hsa-miR-6776, hsa-miR-6075, hsa-miR-8052, hsa-miR-532, hsa-miR-4791, hsa-miR-320b-1, hsa-miR-548y, hsa-miR-7973, hsa-miR-3136-5p, hsa-miR-606, hsa-miR-500a-3p, hsa-miR-4788, hsa-miR-4769-3p, hsa-miR-299-5p, hsa-miR-4431, hsa-miR-6749-5p, hsa-miR-138-2-3p, hsa-miR-1289-2, hsa-miR-548au, hsa-miR-6850, hsa-miR-561, hsa-miR-34b-5p, hsa-miR-3934-5p, hsa-miR-6739-5p, hsa-miR-4325, hsa-miR-4672, hsa-miR-215-5p, hsa-miR-4685-5p, hsa-miR-3160-1, hsa-miR-3160-2, hsa-miR-6793-5p, hsa-miR-8089, hsa-miR-6081, hsa-miR-892b, hsa-miR-936, hsa-miR-548ag, hsa-miR-345, hsa-miR-548k, hsa-miR-3188, hsa-miR-181b-5p, hsa-let-7e, hsa-miR-4487, hsa-miR-509-3p, hsa-miR-3689a-3p, hsa-miR-4771, hsa-miR-520a-5p, hsa-miR-3150b, hsa-miR-6782-5p, hsa-miR-937-5p, hsa-miR-455-3p, hsa-miR-6865-3p, hsa-miR-4749-5p, hsa-miR-378b, hsa-miR-7706, hsa-miR-4445 and hsa-miR-2355-5p.

57 Differentially Expressed Mature miRNAs with >1.2 Fold Change hsa-miR-548ac, hsa-miR-335-5p, hsa-miR-548x-3p, hsa-miR-548ae, hsa-miR-4708-3p, hsa-miR-16-2-3p, hsa-miR-603, hsa-miR-3613-3p, hsa-miR-4797-5p, hsa-miR-548aj-3p, hsa-miR-450b-5p, hsa-miR-548ap-3p, hsa-miR-1184, hsa-miR-2277-5p, hsa-miR-1323, hsa-miR-548aa, hsa-miR-548t-3p, hsa-miR-221-5p, hsa-miR-190a-3p, hsa-miR-6873-5p, hsa-miR-155-3p, hsa-miR-510-5p, hsa-miR-4313, hsa-miR-4306, hsa-miR-8052, hsa-miR-4791, hsa-miR-7973, hsa-miR-3136-5p, hsa-miR-606, hsa-miR-500a-3p, hsa-miR-4769-3p, hsa-miR-299-5p, hsa-miR-6749-5p, hsa-miR-138-2-3p, hsa-miR-34b-5p, hsa-miR-3934-5p, hsa-miR-6739-5p, hsa-miR-4325, hsa-miR-215-5p, hsa-miR-4685-5p, hsa-miR-6793-5p, hsa-miR-936, hsa-miR-548ag, hsa-miR-548k, hsa-miR-181b-5p, hsa-let-7e, hsa-miR-509-3p, hsa-miR-3689a-3p, hsa-miR-4771, hsa-miR-520a-5p, hsa-miR-6782-5p, hsa-miR-937-5p, hsa-miR-455-3p, hsa-miR-6865- 3p, hsa-miR-4749-5p, hsa-miR-378b and hsa-miR-2355-5p.

28 Differentially Expressed Premature miRNAs with >1.2 Fold Change hsa-miR-520g, hsa-miR-520h, hsa-miR-3910-1, hsa-miR-3616, hsa-miR-8075, hsa-miR-6776, hsa-miR-6075, hsa-miR-532, hsa-miR-320b-1, hsa-miR-548y, hsa-miR-4788, hsa-miR-4431, hsa-miR-1289-2, hsa-miR-548au, hsa-miR-6850, hsa-miR-561, hsa-miR-4672, hsa-miR-3160-1, hsa-miR-3160-2, hsa-miR-8089, hsa-miR-6081, hsa-miR-892b, hsa-miR-345, hsa-miR-3188, hsa-miR-4487, hsa-miR-3150b, hsa-miR-7706 and hsa-miR-4445.

These differentially expressed miRNA sequences are illustrated below in Table 1, along with the reference/housekeeping small RNAs cel-miR-39-3p, U6 and ScaRNA17 used as controls. Cel-miR-39-3p is a spike-in control that demonstrates the stability of the RNA samples. U6 and ScaRNA17 are used as internal controls to normalize the readings of the rest of the miRNAs or candidate miRNAs.

TABLE 1

| microRNA/small RNA name | microRNA Sequence |
|---|---|
| cel-miR-39-3p | UCACCGGGUGUAAAUCAGCUUG (SEQ ID NO: 1) |
| hsa-let-7e | CCCGGGCUGAGGUAGGAGGUUGUAUAGUUGAGGAGGACACCC AAGGAGAUCACUAUACGGCCUCCUAGCUUUCCCCAGG (SEQ ID NO: 2) |
| hsa-miR-1184 | CCUGCAGCGACUUGAUGGCUUCC (SEQ ID NO: 3) |
| hsa-miR-1289-2 | CCACGGUCCUAGUUAAAAAGGCACAUUCCUAGACCCUGCCUC AGAACUACUGAACAGAGUCACUGGGUGUGGAGUCCAGGAAUC UGCAUUUUUACCCCUAUCGCCCCCGCC (SEQ ID NO: 4) |

TABLE 1-continued

| microRNA/small RNA name | microRNA Sequence |
|---|---|
| hsa-miR-1323 | UCAAAACUGAGGGGCAUUUUCU (SEQ ID NO: 5) |
| hsa-miR-138-2-3p | GCUAUUUCACGACACCAGGGUU (SEQ ID NO: 6) |
| hsa-miR-155-3p | CUCCUACAUAUUAGCAUUAACA (SEQ ID NO: 7) |
| hsa-miR-16-2-3p | CCAAUAUUACUGUGCUGCUUUA (SEQ ID NO: 8) |
| hsa-miR-181b-5p | AACAUUCAUUGCUGUCGGUGGGU (SEQ ID NO: 9) |
| hsa-miR-190a-3p | CUAUAUAUCAAACAUAUUCCU (SEQ ID NO: 10) |
| hsa-miR-215-5p | AUGACCUAUGAAUUGACAGAC (SEQ ID NO: 11) |
| hsa-miR-221-5p | ACCUGGCAUACAAUGUAGAUUU (SEQ ID NO: 12) |
| hsa-miR-2277-5p | AGCGCGGGCUGAGCGCUGCCAGUC (SEQ ID NO: 13) |
| hsa-miR-2355-5p | AUCCCCAGAUACAAUGGACAA (SEQ ID NO: 14) |
| hsa-miR-299-5p | UGGUUUACCGUCCCACAUACAU (SEQ ID NO: 15) |
| hsa-miR-3136-5p | CUGACUGAAUAGGUAGGGUCAUU (SEQ ID NO: 16) |
| hsa-miR-3150b | GAGGGAAAGCAGGCCAACCUCGAGGAUCUCCCCAGCCUUGGC<br>GUUCAGGUGCUGAGGAGAUCGUCGAGGUUGGCCUGCUUCCCC<br>UC (SEQ ID NO: 17) |
| hsa-miR-3160-1 | GGACCUGCCCUGGGCUUUCUAGUCUCAGCUCUCCUCCAGCUC<br>AGCUGGUCAGGAGAGCUGAGACUAGAAAGCCCAGGGCAGGUU<br>C (SEQ ID NO: 18) |
| hsa-miR-3160-2 | ACCUGCCCUGGGCUUUCUAGUCUCAGCUCUCCUGACCAGCUG<br>AGCUGGAGGAGAGCUGAGACUAGAAAGCCCAGGGCAGGU<br>(SEQ ID NO: 19) |
| hsa-miR-3188 | GGCGCCUCCUGCUCUGCUGUGCCGCCAGGGCCUCCCCUAGCGC<br>GCCUUCUGGAGAGGCUUUGUGCGGAUACGGGGCUGGAGGCCU<br>(SEQ ID NO: 20) |
| hsa-miR-320b-1 | AAUUAAUCCCUCUCUUUCUAGUUCUUCCUAGAGUGAGGAAAA<br>GCUGGGUUGAGAGGGCAAACAAAUUAACUAAUUAAUU<br>(SEQ ID NO: 21) |
| hsa-miR-335-5p | UCAAGAGCAAUAACGAAAAAUGU (SEQ ID NO: 22) |
| hsa-miR-345 | ACCCAAACCCUAGGUCUGCUGACUCCUAGUCCAGGGCUCGUG<br>AUGGCUGGUGGGCCCUGAACGAGGGGUCUGGAGGCCUGGGUU<br>UGAAUAUCGACAGC (SEQ ID NO: 23) |
| hsa-miR-34b-5p | UAGGCAGUGUCAUUAGCUGAUUG (SEQ ID NO: 24) |
| hsa-miR-3613-3p | ACAAAAAAAAAAGCCCAACCCUUC (SEQ ID NO: 25) |
| hsa-miR-3616 | UGUCACUCCGCCAGCAUCAUGAAGUGCACUCAUGAUAUGUUU<br>GCCCCAUCAGCGUGUCACGAGGGCAUUUCAUGAUGCAGGCGG<br>GGUUGGCA (SEQ ID NO: 26) |
| hsa-miR-3689a-3p | CUGGGAGGUGUGAUAUCGUGGU (SEQ ID NO: 27) |
| hsa-miR-378b | ACUGGACUUGGAGGCAGAA (SEQ ID NO: 28) |
| hsa-miR-3910-1 | CUUUUGCUGUCAGUUUUUCUGUUGCUUGUCUUGGUUUUAUGC<br>CUUUUAUAUCAAGGCACAUAAAAGGCAUAAAAACCAAGACAAG<br>CAACAAAAAAAGGAUUGAUCACAGAAG (SEQ ID NO: 29) |
| hsa-miR-3934-5p | UCAGGUGUGGAAACUGAGGCAG (SEQ ID NO: 30) |
| hsa-miR-4306 | UGGAGAGAAAGGCAGUA (SEQ ID NO: 31) |
| hsa-miR-4313 | AGCCCCCUGGCCCCAAACCC (SEQ ID NO: 32) |
| hsa-miR-4325 | UUGCACUUGUCUCAGUGA (SEQ ID NO: 33) |
| hsa-miR-4431 | UGGUUUGCGACUCUGAAAACUAGAAGGUUUAUGACUGGGCA<br>UUUCUCACCCAAUGCCCAAUAUUGAACUUUCUAGUUGUCAGA<br>GUCAUUAACCC (SEQ ID NO: 34) |

TABLE 1-continued

| microRNA/small RNA name | microRNA Sequence |
| --- | --- |
| hsa-miR-4445 | UUCCUGCAGAUUGUUUCUUUUGCCGUGCAAGUUUAAGUUUUU GCACGGCAAAAGAAACAAUCCAGAGGGU (SEQ ID NO: 35) |
| hsa-miR-4487 | ACUGUCCUUCAGCCAGAGCUGGCUGAAGGGCAGAAGGGAACU XGUCCUUCAGCCAGAGCUGGCUGAAGGGCAGA (SEQ ID NO: 36) |
| hsa-miR-450b-5p | UUUUGCAAUAUGUUCCUGAAUA (SEQ ID NO: 37) |
| hsa-miR-455-3p | GCAGUCCAUGGGCAUAUACAC (SEQ ID NO: 38) |
| hsa-miR-4672 | GGCUGCUUCUCGCCUCUGUCCAGCUGUGUGGCCUUGGACAAG CCUCUUGGUUACACAGCUGGACAGAGGCACGAAACAGCC (SEQ ID NO: 39) |
| hsa-miR-4685-5p | CCCAGGGCUUGGAGUGGGGCAAGGUU (SEQ ID NO: 40) |
| hsa-miR-4708-3p | AGCAAGGCGGCAUCUCUCUGAU (SEQ ID NO: 41) |
| hsa-miR-4749-5p | UGCGGGACAGGCCAGGGCAUC (SEQ ID NO: 42) |
| hsa-miR-4769-3p | UCUGCCAUCCUCCCUCCCCUAC (SEQ ID NO: 43) |
| hsa-miR-4771 | AGCAGACUUGACCUACAAUUA (SEQ ID NO: 44) |
| hsa-miR-4788 | AAUGAAGGAUUACGGACCAGCUAAGGGAGGCAUUAGGAUCCU UAUUCUUGCCUCCCUUAGUUGGUCCCUAAUCCUUCGUU (SEQ ID NO: 45) |
| hsa-miR-4791 | UGGAUAUGAUGACUGAAA (SEQ ID NO: 46) |
| hsa-miR-4797-5p | GACAGAGUGCCACUUACUGAA (SEQ ID NO: 47) |
| hsa-miR-500a-3p | AUGCACCUGGGCAAGGAUUCUG (SEQ ID NO: 48) |
| hsa-miR-509-3p | UGAUUGGUACGUCUGUGGGUAG (SEQ ID NO: 49) |
| hsa-miR-510-5p | UACUCAGGAGAGUGGCAAUCAC (SEQ ID NO: 50) |
| hsa-miR-520a-5p | CUCCAGAGGGAAGUACUUUCU (SEQ ID NO: 51) |
| hsa-miR-520g | UCCCAUGCUGUGACCCUCUAGAGGAAGCACUUUCUGUUUGUU GUCUGAGAAAAAACAAAGUGCUUCCCUUUAGAGUGUUACCGU UUGGGA (SEQ ID NO: 52) |
| hsa-miR-520h | UCCCAUGCUGUGACCCUCUAGAGGAAGCACUUUCUGUUUGUU GUCUGAGAAAAAACAAAGUGCUUCCCUUUAGAGUUACUGUUU GGGA (SEQ ID NO: 53) |
| hsa-miR-532 | CGACUUGCUUUCUCUCCUCCAUGCCUUGAGUGUAGGACCGUU GGCAUCUUAAUUACCCUCCCACACCCAAGGCUUGCAGAAGAG CGAGCCU (SEQ ID NO: 54) |
| hsa-miR-548aa | AAAAACCACAAUUACUUUUGCACCA (SEQ ID NO: 55) |
| hsa-miR-548ac | CAAAAACCGGCAAUUACUUUUG (SEQ ID NO: 56) |
| hsa-miR-548ae | CAAAAACUGCAAUUACUUUCA (SEQ ID NO: 57) |
| hsa-miR-548ag | AAAGGUAAUUGUGGUUUCUGC (SEQ ID NO: 58) |
| hsa-miR-548aj-3p | UAAAAACUGCAAUUACUUUUA (SEQ ID NO: 59) |
| hsa-miR-548ap-3p | AAAAACCACAAUUACUUUU (SEQ ID NO: 60) |
| hsa-miR-548au | AAAAGUAAUUGCGGUUUUUGCUAUUGGUUUUAAUGGCAGUU ACUUUUGCACCAG (SEQ ID NO: 61) |
| hsa-miR-548k | AAAAGUACUUGCGGAUUUUGCU (SEQ ID NO: 62) |
| hsa-miR-548t-3p | AAAAACCACAAUUACUUUUGCACCA (SEQ ID NO: 63) |
| hsa-miR-548x-3p | UAAAAACUGCAAUUACUUUC (SEQ ID NO: 64) |
| hsa-miR-548y | GCCUAAACUAUUAGGUUGGUGCAAAAGUAAUCACUGUUUUU GCCAUUACUCUCAGUGGCAAAAACCGUGAUUACUUUUGCACC AACCUAGUAACACCUUCACUGUGGGGG (SEQ ID NO: 65) |

TABLE 1-continued

| microRNA/small RNA name | microRNA Sequence |
|---|---|
| hsa-miR-561 | CUUCAUCCACCAGUCCUCCAGGAACAUCAAGGAUCUUAAACU UUGCCAGAGCUACAAAGGCAAAGUUUAAGAUCCUUGAAGUUC CUGGGGGAACCAU (SEQ ID NO: 66) |
| hsa-miR-603 | CACACACUGCAAUUACUUUUGC (SEQ ID NO: 67) |
| hsa-miR-606 | AAACUACUGAAAAUCAAAGAU (SEQ ID NO: 68) |
| hsa-miR-6075 | GACACCACAUGCUCCUCCAGGCCUGCCUGCCCUCCAGGUCAU GUUCCAGUGUCCCACAGAUGCAGCACCACGGCCCAGGCGGCA UUGGUGUCACC (SEQ ID NO: 69) |
| hsa-miR-6081 | CCACCACGGUGCUGGCACCAGGGCCUCUGCCCCGUAGGACAC CGAGGCUUAUGAAUAGGAGCAGUGCCGGCCAAGGCGCCGGCA CCAUCUUGGUGAU (SEQ ID NO: 70) |
| hsa-miR-6739-5p | UGGGAAAGAGAAAGAACAAGUA (SEQ ID NO: 71) |
| hsa-miR-6749-5p | UCGGGCCUGGGGUUGGGGGAGC (SEQ ID NO: 72) |
| hsa-miR-6776 | CGGGCUCUGGGGUGCAGUGGGGGUUCCCACGCCGCGGCAACCA CCACUGUCUCUCCCCAG (SEQ ID NO: 73) |
| hsa-miR-6782-5p | UAGGGGUGGGGGAAUUCAGGGGUGU (SEQ ID NO: 74) |
| hsa-miR-6793-5p | UCCCCAACCCCUGCCCGCAG (SEQ ID NO: 75) |
| hsa-miR-6850 | GUGCGGAACGCUGGCCGGGGCGGGAGGGGAAGGGACGCCCGG CCGGAACGCCGCACUCACG (SEQ ID NO: 76) |
| hsa-miR-6865-3p | ACACCCUCUUUCCCUACCGCC (SEQ ID NO: 77) |
| hsa-miR-6873-5p | CAGAGGGAAUACAGAGGGCAAU (SEQ ID NO: 78) |
| hsa-miR-7706 | UGGAGCUGUGUGCAGGGCCAGCGCGGAGCCCGAGCAGCCGCG GUGAAGCGCCUGUGCUCUGCCGAGA (SEQ ID NO: 79) |
| hsa-miR-7973 | UGUGACCCUAGAAUAAUUAC (SEQ ID NO: 80) |
| hsa-miR-8052 | CGGGACUGUAGAGGGCAUGAGC (SEQ ID NO: 81) |
| hsa-miR-8075 | CCUUGCUGAUGGCAGAUGUCGGAUCUGCCUCGCUUAUACGUG CCCUUGCUGAUGGCAGAUGUCGGGUCUGCCUCGCUUAU (SEQ ID NO: 82) |
| hsa-miR-8089 | AAGGAGCACUCACUCCAAUUUCCCUGGACUGGGGGCAGGCUG CCACCUCCUGGGGACAGGGGAUUGGGGCAGGAUGUUCCAG (SEQ ID NO: 83) |
| hsa-miR-892b | UGCAAUGCCCUACUCAGAAAGGUGCCAUUUAUGUAGAUUUUA UGUCACUGGCUCCUUUCUGGGUAGAGCAAGGCUCA (SEQ ID NO: 84) |
| hsa-miR-936 | ACAGUAGAGGGAGGAAUCGCAG (SEQ ID NO: 85) |
| hsa-miR-937-5p | GUGAGUCAGGGUGGGGCUGG (SEQ ID NO: 86) |
| scaRNA17 | AGAGGCUUGGGCCGCCGAGCUGGACCCGGACCGGUUUUGGGU ACUGUACUGGGGGCAGGGCAGAGAGGG (SEQ ID NO: 87) |
| U6 | GUGCUCGCUUCGGCAGCACAUAUACUAAAAUUGGAACGAUAC AGAGAAGAUUAGCAUGGCCCCUGCGCAAGGAUGACACGCAAA UUCGUGAAGCGUUCCAUAUUUU (SEQ ID NO: 88) |

Example 1: Expression of Human Mature miRNAs by qPCR in Sample Cohort of 45 AD Patients and 182 Controls The mean log fold change for hsa-miR-335-5p, hsa-miR-3613-3p and hsa-miR-6865-3p PARKmiRs between AD patients and healthy controls are illustrated in FIG. 1. Specificity of PARKmiRs. Plot for qRT-PCR data showing distinct expression (log) patterns observed for PARKmiRs in 50 AD patient serum samples as compared to 182 control serum samples.

Figure 2:
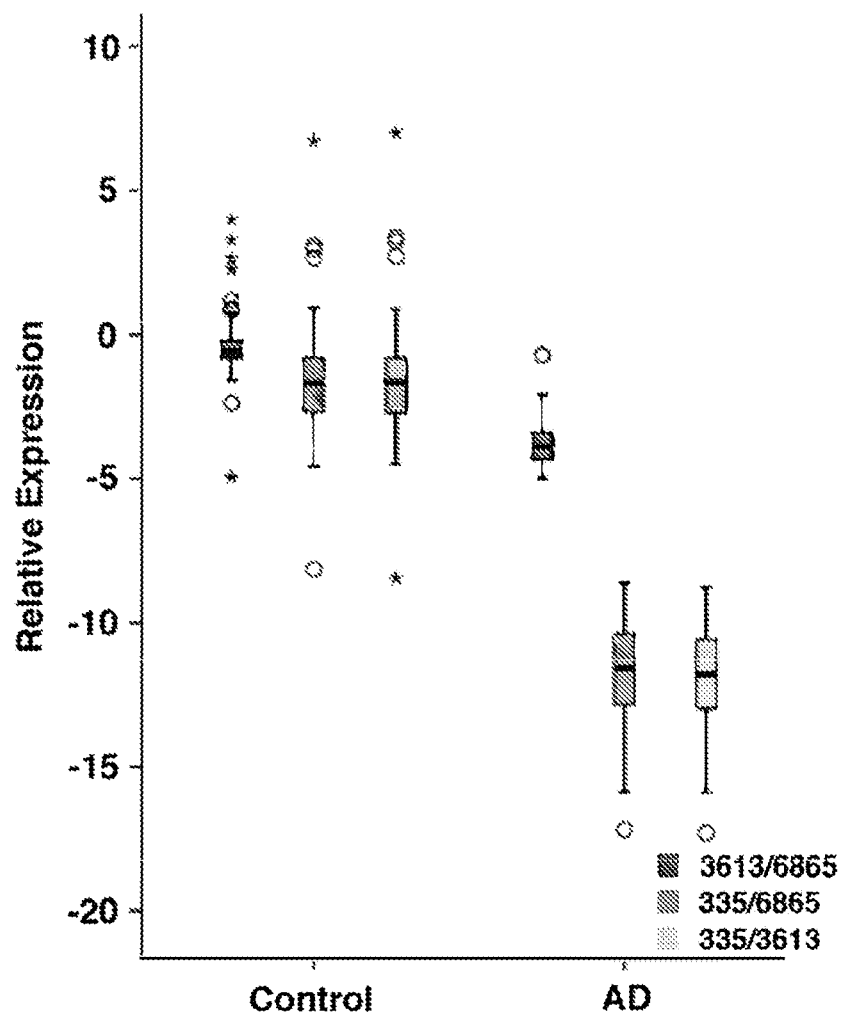
FIG. 2 shows the mean fold change of three combinations of PARKmiRNAs between AD patients and healthy controls.

Example 2: Analyses of PARKmiR Combinations,
hsa-miR-335-5p/hsa-miR-3613-3p, hsa-miR-3613-
3p/hsa-miR-6865-3p and hsa-miR-335-5p/hsa-miR-
6865-3p in Sample Cohort of 45 AD Patients and
182 Controls The qPCR technique of Example 1 was used to identify potential diagnostic biomarkers. It was determined that combinations of PARKmiRs show high predictability for AD diagnosis. The results of the model with hsa-miR-335-5p/hsa-miR-6865-3p, hsa-miR-335-5p/hsa-miR-3613-3p and hsa-miR-6865-3p/hsa-miR-3613-3p between AD patients and healthy controls are illustrated in FIG. 2. Specificity of PARKmiR combinations. Plot for qRT-PCR data showing distinct expression (log) patterns observed for PARKmiR combinations in 50 AD patient serum samples as compared to 182 control serum samples.

Example 3: It is evidenced that any combination of three or more microRNAs from the list of 85 identified miRNAs can be used to diagnose the occurrence of AD in patients.

Example 4: Measurement of levels of a combination of two or more miRNAs in serum from patients can assist in distinctly differentiating between a potential AD patient and a healthy individual. A serum sample is obtained from blood withdrawn from patients suspected of AD. The serum is used for total microRNA isolation and enrichment. This RNA would then be tested using qPCR to measure the levels of any two or more of the 85 miRNAs mentioned in Example 1, or any one of three miRNAs mentioned in Examples 5-7. Detectable levels of any two or more of the 85 miRNAs or any one of the three miRNAs confirms the patient has AD. If desired, other sample fluids may be utilized, including plasma, venous or arterial blood, or CSF samples withdrawn by lumbar puncture. Such plasma, blood or CSF samples are processed as discussed above regarding serum, e.g., so as to provide a sample for processing and evaluation outside the human or animal body. It will be understood that measurement of more than two miRNAs in combination or a set of combinations used in a test matrix may desirably increase the accuracy of AD diagnosis. Following diagnosis, the result is then communicated to the patient.

Example 5: Since a combination of miRNA can be used for diagnosis it may be advisable to test all the candidates to eliminate any cohort-based variation. It is understood that any detectable amounts of relevant miRNA will indicate AD pathology. However, those of ordinary skill in the art recognize it may be clinically helpful to use values of 45 v 182 samples to set an artificial threshold for diagnosis. Differential miRNA levels can be used to develop diagnostic biomarker kits that can be used by clinicians in diagnosis as well as in clinical trials. In this study the presence and quantification of miRNA from serum was determined by qRT-PCR which amplifies and quantifies the RNA is question. Other suitable techniques known to those of ordinary skill herein may be alternatively utilized, including use of labeled antisense sequences and labeled antibodies. Suitable antibodies are preferentially selective, referring to a binding reaction between two molecules that is typically more than 10 to 100 times background molecular associations under measurement conditions. Thus, under designated immunoassay conditions, the specified antibodies bind to a particular miRNA sequence, thereby identifying its presence. Specific binding to an antibody under such conditions requires an antibody that is selected for its specificity for a particular miRNA. For example, antibodies raised against a particular miRNA can be selected by subtracting out antibodies that cross-react with other molecules. A variety of immunoassay formats may be used to select antibodies specifically immunoreactive with a particular miRNA including solid-phase ELISA immunoassays (see, e.g., Harlow & Lane, Antibodies, A Laboratory Manual (1988) for a description of immunoassay formats and conditions that can be used to determine specific immunoreactivity). Methods for determining whether two molecules specifically interact are disclosed therein, and methods of determining binding affinity and specificity are well known in the art (see, for example, Harlow and Lane, Antibodies: A laboratory manual (Cold Spring Harbor Laboratory Press, 1988); Friefelder, "Physical Biochemistry: Applications to biochemistry and molecular biology" (W. H. Freeman and Co. 1976)). The term "antibody" as used herein encompasses naturally occurring antibodies as well as non-naturally occurring antibodies, including, for example, single chain antibodies, chimeric, bifunctional and humanized antibodies, as well as antigen-binding fragments thereof, (e.g., Fab', F(ab')2, Fab, Fv and rIgG). See also, Pierce Catalog and Handbook, 1994-1995 (Pierce Chemical Co., Rockford, IL). See also, e.g., Kuby, J., Immunology, 3rd Ed., W. H. Freeman & Co., New York (1998). Such non-naturally occurring antibodies can be constructed using solid phase peptide synthesis, can be produced recombinantly or can be obtained, for example, by screening combinatorial libraries consisting of variable heavy chains and variable light chains as described by Huse et al., Science, Vol. 246 (1989) 1275-81. These and other methods of making, for example, chimeric, humanized, CDR-grafted, single chain, and bifunctional antibodies are well known to those skilled in the art (Winter and Harris, Immunol. Today, Vol. 14 (1993) 243-46; Ward et al., Nature, Vol. 341 (1989) 544-46; Harlow and Lane, supra, 1988; Hilyard et al., Protein Engineering: A practical approach (IRL Press 1992); Borrabeck, Antibody Engineering, 2d ed. (Oxford University Press 1995). Methods for producing both monoclonal and polyclonal antibodies from identified RNA sequences are well known in the art.

Example 6

Many neurodegenerative diseases are closely related to each other when it comes to symptoms as well as pathological markers. The circulating diagnostic markers for one neurodegenerative disease can be useful for diagnosis of other disease. A method to diagnose other neurodegenerative diseases like Parkinson's Disease, Dementia with Lewy body (DLB), Amyotrophic lateral sclerosis (ALS), Multiple system atrophy (MSA), CorticoBasal Degeneration (CBD), Progressive Supranuclear Palsy (PSP) can also be developed using similar miRNA measurements of candidates mentioned above. Disease specific kits can be developed similar to that mentioned above with various combinations of miRNAs listed in [0019].

Example 7

The miRNAs detected in one or more combinations can regulate several proteins in the cells. Novel protein targets for AD can be discovered using these microRNAs and their combinations. The involvement of these proteins in AD etiology can be further established to target them for therapy.

Example 8

We have experimentally confirmed the predicted regulation of LRRK2 by hsa-miR-335-5p and SNCA by hsa-miR-3613-3p in dopaminergic neuronal cell lines. Therapeutic intervention to regulate the novel targets mentioned can be achieved by RNA interference technologies.

Example 9

Small nucleic acid molecules derived from miRNAs mentioned above will be designed to therapeutically intervene by specifically targeting genes in AD brains to achieve complete or partial remedy. The effects discussed above will be achieved for precise targeting in brain cells.

What is claimed is:

1. A method, comprising the steps of:
   (a) providing a serum sample from a human patient;
   (b) detecting levels of SEQ ID NO: 22 and SEQ ID NO: 77 in the serum sample;
   (c) diagnosing the human patient with Alzheimer's disease when the levels of SEQ ID NO: 22 and SEQ ID NO: 77 in the serum sample are decreased in comparison to the levels of SEQ ID NO: 22 and SEQ ID NO: 77 in control serum samples obtained from healthy patients; and
   (d) administering a cholinesterase inhibitor or an N-methyl-D-aspartate receptor antagonist to said human patient diagnosed with Alzheimer's disease.

2. The method of claim 1, further comprising detecting the level of one or more miRNA selected from the group consisting of SEQ ID NOS: 2-21, 23, 24, 25-76 and 78-86 within said serum sample.

3. The method of claim 2, wherein said one or more miRNA comprises SEQ ID NO: 15.

4. The method of claim 2, wherein said one or more miRNA comprises SEQ ID NO: 21.

5. The method of claim 2, wherein said one or more miRNA comprises SEQ ID NO: 24.

6. The method of claim 2, wherein said one or more miRNA comprises SEQ ID NO: 52.

7. The method of claim 2, wherein said one or more miRNA comprises SEQ ID NO: 54.

8. The method of claim 2, wherein said one or more miRNA comprises SEQ ID NO: 55.

9. The method of claim 1, further comprising detecting the level of one or more miRNA selected from the group consisting of SEQ ID NOS: 2, 3, 5, 6, 7, 8, 9, 10, 11, 12, 13, 14, 15, 16, 24, 25, 26, 27, 28, 31, 30, 32, 33, 37, 38, 40, 42, 43, 44, 46, 47, 48, 49, 50, 51, 55, 56, 57, 58, 59, 60, 62, 63, 64, 67, 68, 71, 72, 74, 75, 78, 80, 81, 85 and 86 within said serum sample.

10. The method of claim 1, further comprising detecting the level of one or more miRNA selected from the group consisting of SEQ ID NOS: SEQ ID NOS: 4, 17, 18, 19, 20, 21, 23, 25, 26, 29, 34, 35, 36, 39, 45, 52, 53, 54, 61, 65, 66, 69, 70, 73, 76, 79, 82, 83 and 84 within said serum sample.

11. The method of claim 1, further comprising detecting the level of one or more miRNA selected from the group consisting of SEQ ID NOS: 15, 21, 24, 52, 54 and 55 within said serum sample.

12. The method of claim 1, further comprising detecting the level of one or more miRNA selected from the group consisting of SEQ ID NOS: 2-21, 23, 24, 25-76 and 78-86 within said serum sample.

13. The method of claim 1, further comprising detecting the level of one or more miRNA selected from the group consisting of SEQ ID NOS: 2, 3, 5, 6, 7, 8, 9, 10, 11, 12, 13, 14, 15, 16, 24, 25, 26, 27, 28, 31, 30, 32, 33, 37, 38, 40, 42, 43, 44, 46, 47, 48, 49, 50, 51, 55, 56, 57, 58, 59, 60, 62, 63, 64, 67, 68, 71, 72, 74, 75, 78, 80, 81, 85 and 86 within said serum sample.

14. The method of claim 1, further comprising detecting the level of one or more miRNA selected from the group consisting of SEQ ID NOS: 4, 17, 18, 19, 20, 21, 23, 25, 26, 29, 34, 35, 36, 39, 45, 52, 53, 54, 61, 65, 66, 69, 70, 73, 76, 79, 82, 83 and 84 within said serum sample.

15. The method of claim 1, further comprising detecting the level of one or more miRNA selected from the group consisting of SEQ ID NOS: 15, 21, 24, 52, 54 and 55 within said serum sample.

16. The method of claim 1, wherein said cholinesterase inhibitor is donepezil, galantamine or rivastigmine.

17. The method of claim 1, wherein said N-methyl-D-aspartate receptor antagonist is memantine.

18. The method of claim 1, wherein said one or more miRNA comprises SEQ ID NO: 25.

19. The method of claim 18, further comprising detecting the level of one or more miRNA selected from the group consisting of SEQ ID NOS: 2-21, 23, 24, 26-76 and 78-86 within said serum sample.

20. The method of claim 19, wherein said at least one or more miRNA comprises SEQ ID NO: 15.

21. The method of claim 19, wherein said at least one or more miRNA comprises SEQ ID NO: 21.

22. The method of claim 19, wherein said at least one or more miRNA comprises SEQ ID NO: 24.

23. The method of claim 19, wherein said at least one or more miRNA comprises SEQ ID NO: 52.

24. The method of claim 19, wherein said at least one or more miRNA comprises SEQ ID NO: 54.

25. The method of claim 19, wherein said at least one or more miRNA comprises SEQ ID NO: 55.

26. The method of claim 18, further comprising detecting the level of at least one or more miRNA selected from the group consisting of SEQ ID NOS: 2, 3, 5, 6, 7, 8, 9, 10, 11, 12, 13, 14, 15, 16, 24, 26, 27, 28, 31, 30, 32, 33, 37, 38, 40, 42, 43, 44, 46, 47, 48, 49, 50, 51, 55, 56, 57, 58, 59, 60, 62, 63, 64, 67, 68, 71, 72, 74, 75, 78, 80, 81, 85 and 86 within said serum sample.

27. The method of claim 18, further comprising detecting the level of at least one or more miRNA selected from the group consisting of SEQ ID NOS: SEQ ID NOS: 4, 17, 18, 19, 20, 21, 23, 26, 29, 34, 35, 36, 39, 45, 52, 53, 54, 61, 65, 66, 69, 70, 73, 76, 79, 82, 83 and 84 within said serum sample.

28. The method of claim 18, further comprising detecting the level of at least one or more miRNA selected from the group consisting of SEQ ID NOS: 15, 21, 24, 52, 54 and 55 within said serum sample.

29. The method of claim 18, further comprising detecting the level of at least two or more miRNAs selected from the group consisting of SEQ ID NOS: 2-21, 23, 24, 26-76 and 78-86 within said serum sample.

30. The method of claim 18, further comprising detecting the level of at least two or more miRNAs selected from the group consisting of SEQ ID NOS: 2, 3, 5, 6, 7, 8, 9, 10, 11, 12, 13, 14, 15, 16, 24, 26, 27, 28, 31, 30, 32, 33, 37, 38, 40, 42, 43, 44, 46, 47, 48, 49, 50, 51, 55, 56, 57, 58, 59, 60, 62, 63, 64, 67, 68, 71, 72, 74, 75, 78, 80, 81, 85 and 86 within said serum sample.

31. The method of claim 18, further comprising detecting the level of at least two further miRNAs selected from the group consisting of SEQ ID NOS: 4, 17, 18, 19, 20, 21, 23, 26, 29, 34, 35, 36, 39, 45, 52, 53, 54, 61, 65, 66, 69, 70, 73, 76, 79, 82, 83 and 84 within said serum sample.

32. The method of claim 18, further comprising detecting the levels of at least two or more miRNAs selected from the group consisting of SEQ ID NOS: 15, 21, 24, 52, 54 and 55 within said serum sample.

33. The method of claim 18, wherein said cholinesterase inhibitor is donepezil, galantamine or rivastigmine.

34. The method of claim 18, wherein said N-methyl-D-aspartate receptor antagonist is memantine.

* * * * *